(12) United States Patent
Engelhardt et al.

(10) Patent No.: US 8,559,021 B2
(45) Date of Patent: Oct. 15, 2013

(54) THREE-DIMENSIONALLY LOCALIZING LIGHT EMITTING MOLECULES OF UNKNOWN ORIENTATION AND UNKNOWN Z-POSITION

(75) Inventors: Johann Engelhardt, Bad Schoenborn (DE); Stefan W. Hell, Goettingen (DE); Jan Keller-Findeisen, Geottingen (DE)

(73) Assignees: Deutsches Krebsforschungszentrum, Heidelberg (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/441,043

(22) Filed: Apr. 6, 2012

(65) Prior Publication Data
US 2012/0212750 A1 Aug. 23, 2012

Related U.S. Application Data

(63) Continuation of application No. PCT/EP2010/064989, filed on Oct. 7, 2010.

(30) Foreign Application Priority Data

Oct. 9, 2009 (EP) ..................................... 09172670

(51) Int. Cl.
G01B 11/14 (2006.01)
G01J 3/30 (2006.01)
G06K 9/00 (2006.01)

(52) U.S. Cl.
USPC ........... 356/623; 356/317; 356/614; 356/624; 382/128

(58) Field of Classification Search
None
See application file for complete search history.

(56) References Cited

U.S. PATENT DOCUMENTS 1,957,371 A * 5/1934 Thomas ........................... 353/33
4,573,195 A * 2/1986 de France ...................... 382/133

(Continued)

FOREIGN PATENT DOCUMENTS

| JP | 10177738 A | * | 6/1998 |
| JP | 11039699 A | * | 2/1999 |
| SU | 699470 A | * | 11/1979 |

OTHER PUBLICATIONS

Manuel F. Juette et al.: "Three-dimensional sub-100 nm resolution fluorescence microscopy of thick samples" in Nature Methods, vol. 5, No. 6, Jun. 2008, p. 527-529.

(Continued)

*Primary Examiner* — Gordon Stock, Jr.
(74) *Attorney, Agent, or Firm* — Thomas | Horstemeyer, LLP

(57) ABSTRACT

To the end of three-dimensionally localizing light emitting marker entities of unknown orientation and unknown position in a sample, the light emitted by each single marker entity is imaged in at least two different ways onto at least one detection plane which corresponds to a focal plane (13) in the sample resulting in at least two images of the marker entity. Virtual x- and y-positions of the marker entity in parallel to the focal plane (13) are separately determined from the emitted light intensity distribution over each image of the marker entity. Further, the z-position of the marker entity normal to the focal plane is determined from the emitted light intensity distributions over the images of the marker entity. The real x- and y-positions of the marker entity in parallel to the focal plane (13) are determined based on its virtual x- and y-positions and on its z-position.

10 Claims, 5 Drawing Sheets

(56) References Cited

U.S. PATENT DOCUMENTS

| | | | | |
|---|---|---|---|---|
| 4,833,315 | A * | 5/1989 | Horikawa | 250/201.7 |
| 4,916,473 | A * | 4/1990 | Mukai et al. | 396/114 |
| 4,954,701 | A * | 9/1990 | Suzuki et al. | 250/201.8 |
| 5,349,592 | A * | 9/1994 | Ando | 372/32 |
| 5,861,987 | A * | 1/1999 | Nakamura et al. | 359/434 |
| 6,034,797 | A * | 3/2000 | Ju et al. | 359/15 |
| 8,284,261 | B2 * | 10/2012 | Mizuo | 348/208.12 |
| 8,309,900 | B1 * | 11/2012 | Marron | 250/208.1 |
| 8,310,652 | B2 * | 11/2012 | Kanayama | 356/4.06 |
| 8,369,579 | B2 * | 2/2013 | Frigerio | 382/107 |
| 2002/0114077 | A1 * | 8/2002 | Javidi | 359/618 |
| 2008/0180792 | A1 * | 7/2008 | Georgiev | 359/368 |
| 2010/0303386 | A1 * | 12/2010 | Enderlein | 382/299 |
| 2011/0128352 | A1 * | 6/2011 | Higgins et al. | 348/46 |
| 2012/0218379 | A1 * | 8/2012 | Ozcan et al. | 348/40 |

OTHER PUBLICATIONS

Erdal Toprak et al.: "Defocused orientation and position imaging (DOPI) of myosin V" in PNAS, Apr. 25, 2006, vol. 103, No. 17, p. 6495-6499.

Jörg Enderlein et al.: "Polarization effect on position accuracy of fluorophore localization" in: Optics Express, vol. 14, No. 18, Sep. 2, 2006, p. 8111-8120.

Alipasha Vaziri et al.: "Multilayer three-dimensional super resolution imaging of thick biological samples" PNAS, vol. 105, No. 51, Dec. 23, 2008, pp. 20221-20226, XP002568452.

Michael J. Mlodzianoski et al.: "Experimental characterization of 3D localization techniques for particle-tracking and super-resolution microscopy", Optics Express, vol. 17, No. 10, May 11, 2009, pp. 8264-8277, XP002568448.

Marta Fernández-Suárez and Alice Y. Ting: "Fluorescent probes for super-resolution imaging in living cells" Nature Reviews Molecular Cell Biology, vol. 9, Dec. 2008, pp. 929-943, XP002582391 DOI: 10.1038/nrm2531.

Scott E. Irvine, Dr. et al.: "Direct Light-Driven Modulation of Luminescence from Mn-Doped ZnSe Quantum Dots" Angewandte Chemie International Edition, vol. 47, No. 14, Feb. 27, 2008, pp. 2685-2688, XP002582392, DOI: 10.1002/anie.200705111.

International search report in copending, related International application No. PCT/EP2010/064989, mailed Dec. 22, 2010.

* cited by examiner

US 8,559,021 B2

THREE-DIMENSIONALLY LOCALIZING LIGHT EMITTING MOLECULES OF UNKNOWN ORIENTATION AND UNKNOWN Z-POSITION

CROSS REFERENCE TO RELATED APPLICATIONS

The present application is a continuation of International Application PCT/EP2010/064989 entitled "Three-Dimensionally localizing Light emitting Molecules of unknown Orientation and unknown Z-Position", filed Oct. 7, 2010, and claims priority to European Patent Application EP 09 172 670.3 entitled "Three-Dimensionally localizing Light emitting Molecules of unknown Orientation and unknown Z-Position" filed Oct. 9, 2009.

FIELD OF THE INVENTION

The invention relates to methods of three-dimensionally localizing light emitting marker entities of unknown orientation and unknown position in a sample. Further, the invention relates to an apparatus for three-dimensionally localizing light emitting marker entities of unknown orientation and unknown z-position in a sample.

The position of a light emitting marker entity of unknown position may be unknown in all three dimensions. i.e. not physically limited to a particular plane of the sample, for example.

The light emitting marker entity may, for example, be a light emitting molecule or another small marker entity useable as a fluorescent dye, like, for example, a Quantum-dot. Thus, the invention is applicable in any kind of fluorescence light microscopy, in which the position or distribution of structures marked with such fluorescent dyes is of interest. Applications of the invention in fluorescence light microscopy, in which the position or distribution of structures marked with such fluorescent dyes is determined in all three dimensions or spatial directions at high spatial resolution, preferably surpassing the diffraction barrier, are of particular interest.

BACKGROUND OF THE INVENTION

A method of and an apparatus for three-dimensionally localizing light emitting marker entities of unknown orientation and unknown position in a sample are known from Manuel F. Juette et al.: "Three-dimensional sub-100 nm resolution fluorescence microscopy of thick samples" in Nature Methods, Vol. 5 No. 6, June 2008, p. 527-529. This paper discloses a method named biplane (BP) FPALM which combines a double-plane detection scheme with fluorescence photo-activation localization microscopy (FPALM) enabling three-dimensional sub-diffraction resolution. The z-position of the light emitting molecules is determined from the light intensity distributions over two detection planes onto which the light emitted by each single molecule is imaged and which correspond to two focal planes arranged at a known distance in z-direction. Depending on the actual position of a particular single molecule in z-direction, the emitted light intensity distributions over the different detection planes show different intensities and patterns allowing to determine the initially unknown z-position. In x- and y-directions in parallel to the focal planes, the position of each single molecule is determined in a way generally known from methods including FPALM, PALM, Stochastic Optical Reconstruction Microscopy (STORM) and PALM with Independently Running Acquisition (PALM IRA). This way principally includes fitting a two-dimensional Gaussian intensity distribution to the detected intensity distributions over the detection plane and defining the centre of the Gaussian distribution as the position of the molecule in x- and y-directions. Manuel F. Juette et al. do not care for any effects due to dipole characteristics of the molecules in emitting light.

From Erdal Toprak et al.: "Defocused orientation and position imaging (DOPI) of myosin V" in PNAS, Apr. 25, 2006, vol. 103 no. 17, p. 6495-6499, it is known that the centroid of a fluorophore can be determined within 1.5 nm accuracy from its focussed image through fluorescence imaging with one-nanometer accuracy (FIONA), and that, if, instead, the sample is moved away from the focus, the point-spread-function depends on both the position and three-dimensional orientation of the fluorophore, which can be calculated by defocused orientation and position imaging (DOPI). By switching back and forth between focussed and defocused imaging, DOPI allows for getting the centroid and the orientation of light emitting entities known to be located in a particular plane. The orientation of the marker entities is obtained from the emitted light intensity distribution of the defocused images of the marker entities; whereas their lateral position in the known plane is determined from the centre of the emitted light intensity distribution in the focussed image. The light emitting marker entities are either fluorophores, i.e. fluorescent molecules or quantum dots.

From Jörg Enderlein et al.: "Polarization effect on position accuracy of fluorophore localization" in: OPTICS EXPRESS, Vol. 14, No. 18, Sep. 2, 2006, p. 8111-8120, it is known that the intensity distribution of a light emitting molecule does not only depend on its position in space, but also on its three-dimensional orientation. Thus, the position determination usually done by fitting at two-dimensional Gaussian (x-y vs. photon number) to the emission intensity distribution may not result in the correct position of the light emitting molecule. In case of molecules placed in water on a glass surface, i.e. at a known z-position, the maximum shift of the centre position determined in this way using a 1.4 N.A. objective, however, was only 16 nm. With a smaller N.A. this position error should even be smaller as it is pointed out that the position accuracy for intermediate inclination angles of the dipole orientation of the light emitting molecules decreases with increasing N.A. Further, it is indicated that, if a dye is able to wobble around its attachment point during image exposure, thus emulating an isotropic emitter, the resulting image will be symmetric with respect to the actual position of the dye, and a 2-D Gaussian fitting will yield better FIONA accuracy than for any of the fixed dipole orientations. Jörg Enderlein et al. explicitly only regard conventional epi-fluoroscence microscopy and lateral positioning accuracy for molecules within the objective's focal plane. Studying the impact of molecule orientation on the position accuracy in other cases is told to be the topic of further studies.

There still is a need of methods of three-dimensionally localizing light emitting marker entities of unknown orientation and unknown position in a sample, and an apparatus for three-dimensionally localizing light emitting molecules of unknown orientation and unknown z-position in a sample in a sample, which provide for accurate x- and y-positions of the marker entities in the sample independently of their actual orientation and their actual z-position.

SUMMARY OF THE INVENTION

The invention relates to a method of three-dimensionally localizing light emitting marker entities of unknown orientation and unknown position in a sample. The method comprises imaging light emitted by each single marker entity in at least two different ways onto at least one detection plane which corresponds to a focal plane in the sample resulting in at least two images of the marker entity. From the emitted light intensity distribution over each image of the marker entity virtual x- and y-positions in parallel to the focal plane of each marker entity are separately determined. A z-position of each marker entity normal to the focal plane is determined from the emitted light intensity distributions over the images of the marker entity; and real x- and y-positions of each marker entity in parallel to the focal plane are determined based on its virtual x- and y-positions and on its z-position.

The invention also relates to an apparatus for three-dimensionally localizing light emitting entities of unknown orientation in a sample, the apparatus comprising an objective imaging light emitted out of a sample on a spatial light detector, wherein the light passing through each of at least two different aperture regions of the objective is focussed in a separate one of at least two laterally offset images.

The invention further relates to a method of three-dimensionally localizing light emitting marker entities of unknown orientation and unknown position in a sample. The method comprises selecting light emitting marker entities from a group of light emitting marker entities which display no dipole characteristics in emitting light; marking a structure of interest in a sample with the selected marker entities; imaging light emitted by each single marker entity in the sample onto at least two detection planes each corresponding to a focal plane in the sample; and determining the x- and y-positions of each marker entity in parallel to the focal planes and the z-position of each marker entity normal to the focal planes from the emitted light intensity distributions over the detection planes.

SHORT DESCRIPTION OF THE DRAWINGS

The invention will be better understood with reference to the accompanied drawings. The components in the drawings are not necessarily to scale, emphasis instead being placed upon clearly illustrating the principles of the present invention. In the drawings, like reference numerals designate corresponding parts throughout the several views.

FIG. 1 is a section in x- and z-direction through an intensity distribution of light emitted by a dipole tilted by 45° with regard to the x-direction and running orthogonal to the y-direction which is normal to the drawing plane. Further, FIG. 1 shows three different sections in x- and y-direction through the emitted light intensity distribution. These three sections correspond to images of the light emitted by the dipole and imaged on different detection planes corresponding to different focal planes arranged at distances in z-direction.

Figure 4:
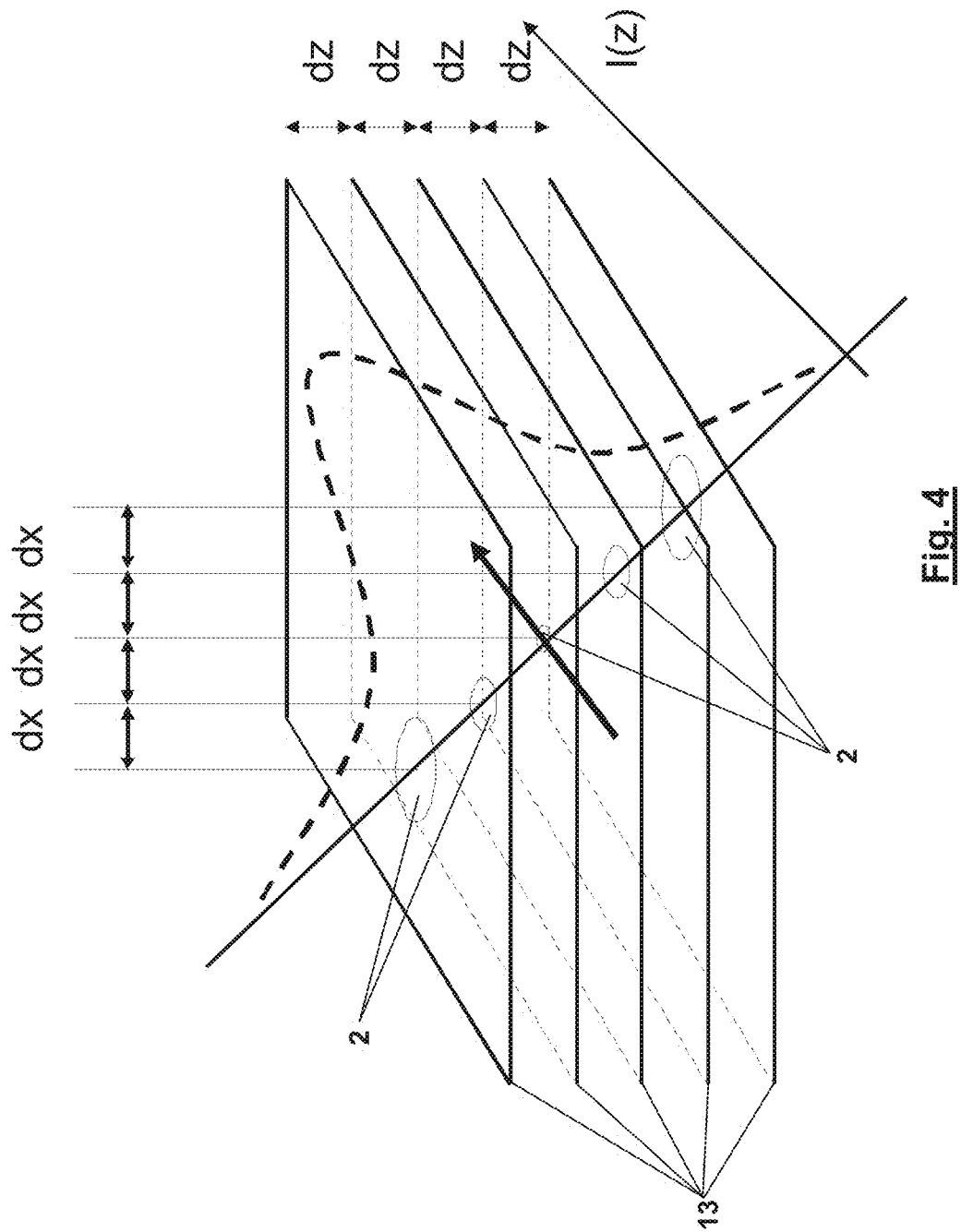
Figure 5:
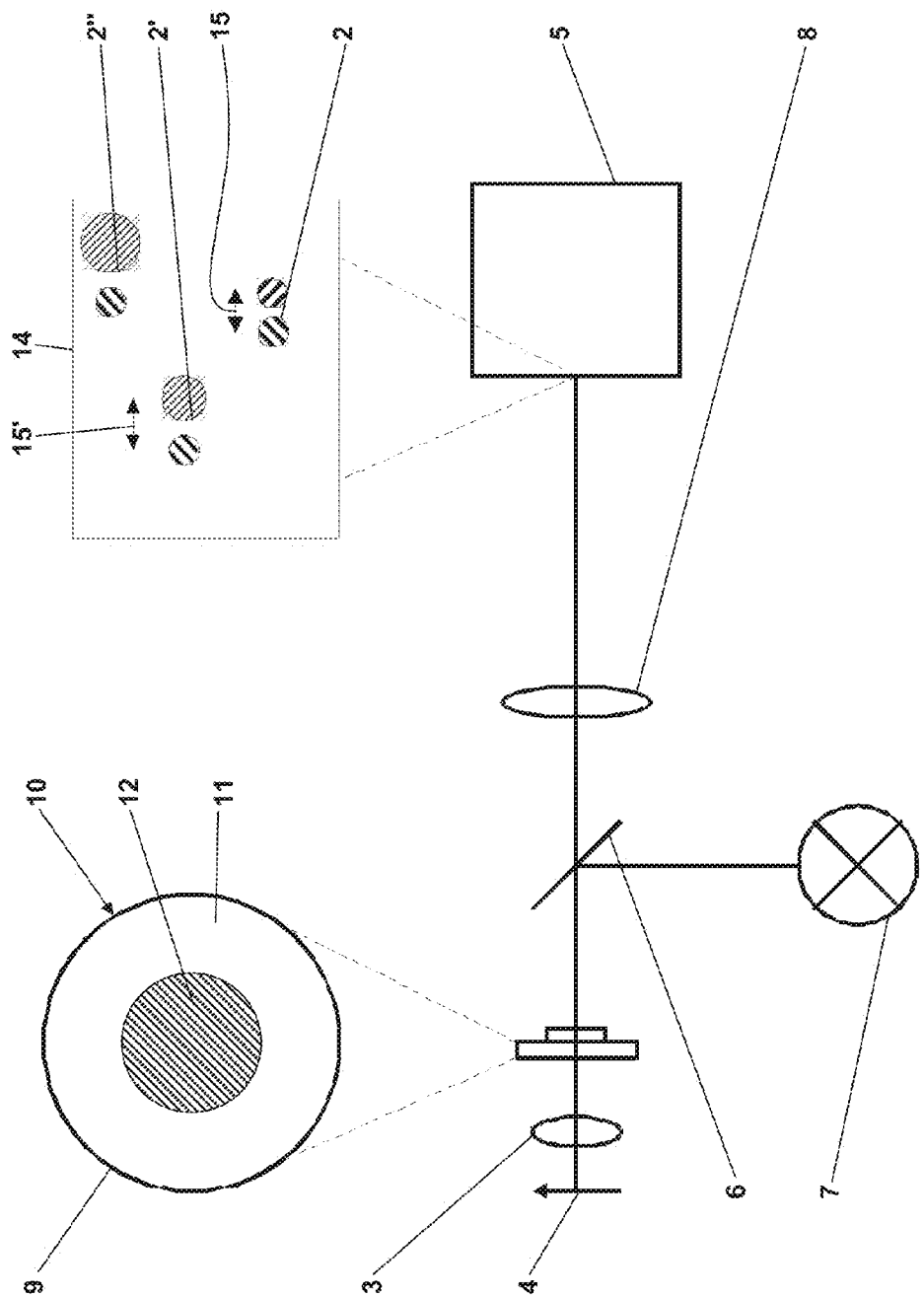

FIG. 4 indicates how multi focal plane imaging of a dipole allow for determining its real position in x- and y-direction based on the light intensity distributions detected in defocused images of the dipole; and FIG. 5 indicates the new apparatus according to the invention and the embodiment of the new method executed with this apparatus in which different numerical apertures are used to visualize the virtual shift in position of an imaged dipole tilted at an angle with regard to the x-y-plane.

DETAILED DESCRIPTION

Based on calculations and confirmed by actual measurements, the inventors have found that the dipole orientation of a light emitting marker entity in a sample which has an unknown axial position, i.e. an unknown z-position, may result in a centre of a two-dimensional Gaussian fit to the light intensity distribution of an image of the emitted light, which deviates by many 10 nm from the real lateral position, i.e. from the real x- and y-positions of the marker entity in the sample. This uncertainty is only present for defocused images of the marker entities. However, with an unknown z-position of the marker entities, a defocus of their images will be the norm. Particularly, the uncertainties due to the unknown position in z-direction and the unknown orientation of the light emitting marker entities may result in totally wrong determinations of the distance between two marker entities with oppositely tilted dipole orientations. Particularly, the uncertainty due to the unknown orientation of the marker entities is much higher than the spatial resolution in x- and y-directions claimed for standard methods of localizing light emitting marker entities in a sample like FPALM, PALM, STORM and PALMIRA. The inventors, however, found ways to resolve this uncertainty.

According to the first method of the present invention, the x- and y-positions of the marker entity determined from the emitted light intensity distribution over each image of the marker entity are only regarded as virtual x- and y-positions. These virtual x- and y-positions of the marker entity are separately determined from the emitted light intensity distribution over each single image of the marker entity, as these virtual x- and x-positions include valuable information on the real x- and y-positions of the marker entity in parallel to the focal plane. In fact, the real x- and y-positions of the marker entity in parallel to the focal plane can be determined based on its virtual x- and y-positions and on its z-position normal to the focal plane.

This z-position may for example be determined according to the known BP FPALM-method in which each single marker entity is images onto at least two detection planes corresponding to at least two focal planes arranges at a known distance in the sample to provide the at least two images of each single marker entity. Thus, the light emitted by each single marker entity may be imaged in at least two different ways resulting in at least two images of the marker entity in the first new method in that each single marker entity is imaged onto at least two detection planes corresponding to at least two focal planes arranged at a known distance in the sample to provide the at least two images of the light emitting marker entity which are evaluated for its position in all three dimensions.

Alternatively, the light emitted by each single marker entity may be imaged in at least two different ways resulting in at least two images of the marker entity in the first new method in that the light emitted by each single marker entity may be separately imaged via at least two different aperture regions of a same objective onto the same detection plane to provide the at least two images. This alternative makes use of the fact that the difference between the virtual and the real x- and y-positions of a defocused marker entity depend on the N.A. of the objective used for imaging the marker entity.

In both embodiments of the first new method, the real x- and y-positions of the marker entity in parallel to the focal plane may be extrapolated for its z-position normal to the focal plane from its virtual x- and y-positions. This extrapolation may simply be a linear one. Even such a simple linear extrapolation reduces the original uncertainty in the x- and y-positions of a light emitting marker entity of unknown orientation to just a small fraction of the original uncertainty.

As the virtual x- and y-positions determined from the emitted light intensity distribution over each image of the marker entity depend on the z-position of the marker entity, they include information on that z-position and may be accounted for in determining the z-position of the molecule normal to the focal plane.

The main information on the z-position of the marker entities, however, is included in the total or peak emitted light intensities in the images of the marker entities. Thus, these total or peak emitted light intensities are preferably accounted for in determining the z-position of the marker entity normal to the focal plane. Here, both the absolute and the relative total or peak emitted light intensities include valuable information and may be evaluated. The absolute total or peak emitted light intensities may be compared with the absolute total or peak emitted light intensity of a light emitting marker intensity of a known defocus and orientation, particularly of a defocus of zero and a dipole orientation in the focal plane, and include information on the defocus and orientation of the actually imaged light emitting marker entity. The relative absolute total or peak emitted light intensities also include information on the defocus and orientation of the actually imaged light emitting marker entity, and point to the direction of the z-position of the light emitting marker entity with regard to the focal plane.

Further information on the z-position of the marker entities normal to the focal plane is included in emitted light intensity patterns in the images of the marker entities. I.e. different z-positions of the marker entities normal to the focal plane result in different emitted light intensity patterns in the images of the marker entities which include information on the actual z-positions of the marker entities.

Actually, both the real x- and y-positions and the z-position plus the dipole direction of the light emitting marker entity may be obtained from the images of the marker entity in that a function $I(x,y,z,p)$ is fitted to the emitted light intensity distributions in the images of the marker entity.

The new method is particularly applicable in three-dimensionally localizing a plurality of light emitting marker entities of unknown orientation in the sample based on an overall emitted light intensity distributions over the at least one detection plane detected during one period of time. Even more particular, different pluralities of light emitting marker entities of unknown orientation in the sample, which are selected by a statistical transfer process between a light emitting state and a no or other light emitting state of the marker entities, may be three-dimensionally localized based on several overall emitted light intensity distributions over the at least one detection plane detected during different periods of time. I.e. the new method may be integrated into any kind of FPALM, PALM, STORM and PALM IRA method.

Whereas an apparatus suitable for BP FPALM is also suitable for the embodiment of the first new method based on the known BP FPALM method, the alternative embodiment of the first new method indicated above requires a new apparatus comprising an objective imaging light emitted out of a sample onto a spatial light detector, which is characterized in that the light passing through at least two different aperture regions of the objective is focussed in at least two laterally offset points. Thus, the two images of each marker entity have a known basic offset in x- and/or y-direction. The deviations of the virtual x- and y-positions from the real x- and y-positions of the marker entity due to a defocus of the images, which also differ with the effective N.A. for the respective image, are superimposed with this basic offset.

In a particular embodiment, the new apparatus comprises an optical element dividing the aperture of the objective in a ring shaped outer region and a circular inner region and which causes a deflection of the light passing through one of these two regions with regard to the light passing through the other of the two regions.

The second new method uses light emitting marker entities displaying no dipole characteristics in emitting light in localizing the light emitting marker entities with unknown orientation. Particularly, these light emitting marker entities displaying no dipole characteristics in emitting light are selected from the group of light emitting marker entities transferable between a light emitting state and a no or other light emitting state to allow for imaging a structure marked by the marker entities according to the basic principles known from FPALM, PALM, STORM or PALMIRA.

Even more particularly, the light emitting marker entities may be selected from the group including nano diamond and Quantum-dot fluorescent dyes. Nano diamond fluorescent dyes display no dipole characteristic in emitting light, and quantum-dot fluorescent dyes are available in embodiments displaying no relevant dipole characteristics in emitting light. A Quantum-dot of symmetric construction in all spatial directions, may, for example still have different emission properties in different spatial directions, but theses differences are only small and neglectable in localizing the Quantum-dot by the emitted light. (There are other Quantum-dot fluorescence dyes which even display strong dipole characteristics and which are thus not suitable for use in the second new method.) Both nano diamond and Quantum-dot fluorescent dyes are known to have a long useable lifetime as compared to other fluorescent dyes, particularly as compared to other switchable fluorescent dyes.

In both new methods, the (virtual) x- and y-positions of the marker entity may be determined from the emitted light intensity distribution over each image of the marker entity in the usual way as the centre of the light intensity distribution, or, more particular, as the centre of a two-dimensional Gaussian fit to the light intensity distribution of an image of the emitted light.

Advantageous developments of the invention result from the claims, the description and the drawings. The advantages of features and of combinations of a plurality of features mentioned at the beginning of the description only serve as examples and may be used alternatively or cumulatively without the necessity of embodiments according to the invention having to obtain these advantages. Further features may be taken from the drawings, in particular from the illustrated designs and the dimensions of a plurality of components with respect to one another as well as from their relative arrangement and their operative connection. The combination of features of different embodiments of the invention or of features of different claims independent of the chosen references of the claims is also possible, and it is motivated herewith. This also relates to features which are illustrated in separate drawings, or which are mentioned when describing them. These features may also be combined with features of different claims. Furthermore, it is possible that further embodiments of the invention do not have the features mentioned in the claims.

Figure 1:
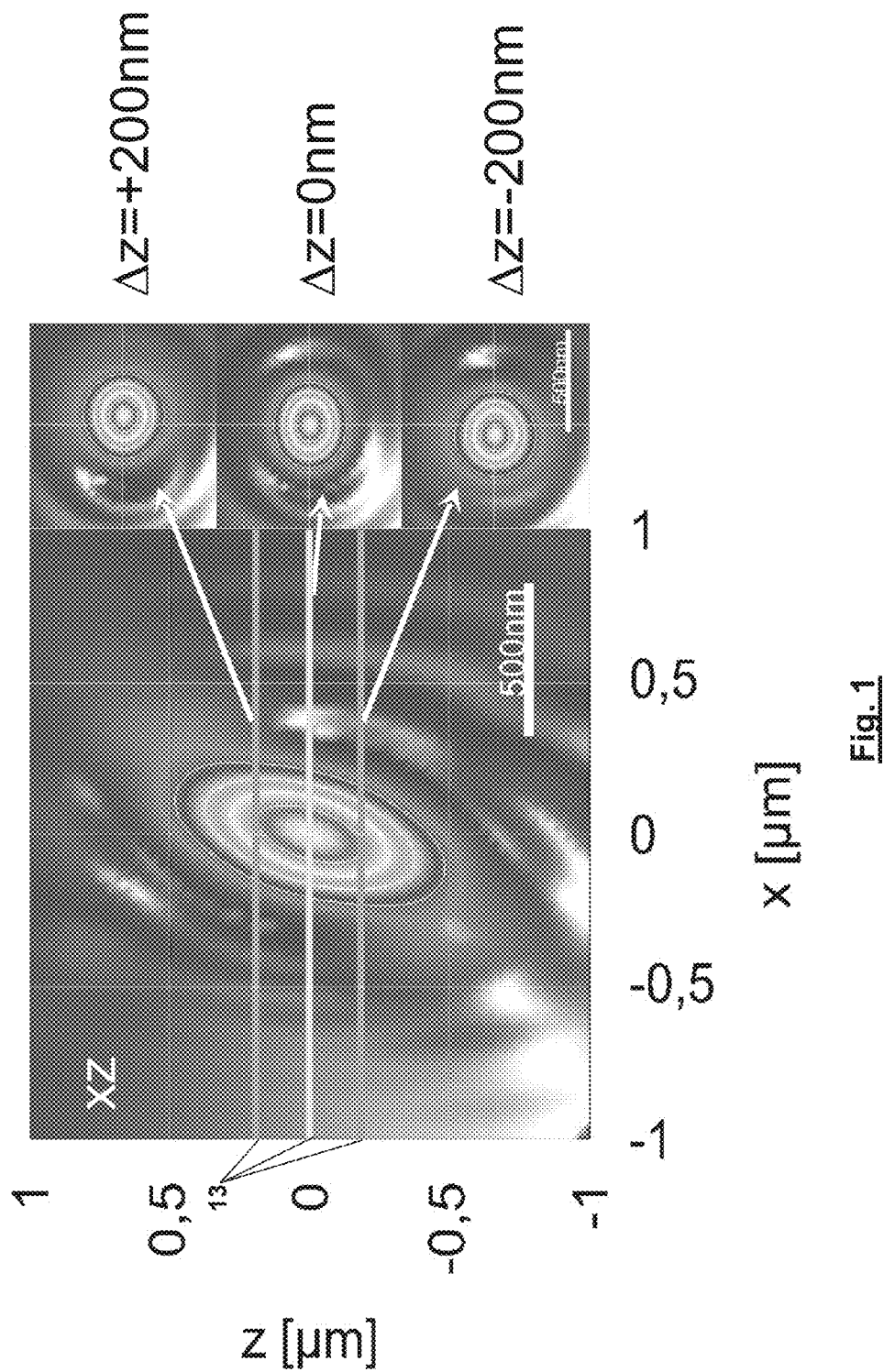

Refering now in greater detail to the drawings, FIG. 1 consists of four pictures. The big one on the left hand side of FIG. 1 is a section in x- and z-direction through the emitted light intensity distribution of a dipole indicating the light intensities detectable at the different points in this x-z-plane having its origin in the centre of the dipole. The brighter a picture point of FIG. 1, the higher is the emitted light intensity which will be measured at that particular point. The light intensity distribution of FIG. 1 is for a dipole having a fixed orientation with a tilt angle of 45° with regard to the x-y-plane and for a fixed numerical aperture (N. A.) in measuring the light intensities. The three smaller pictures at the right hand side of FIG. 1 depict three sections through the emitted light intensity distribution in x- and y-directions at three different levels in z-direction. The picture in the middle is a x-y-section through the centre of the dipole. It indicates the emitted light intensity distribution of a focused picture of the dipole. Here, the centre of the light intensity distribution is the centre of the dipole in x- and y-direction. The upper and lower pictures on the right hand side of FIG. 1, however, correspond to defocused pictures of the dipole with a defocus of +200 nm and −200 nm, respectively. Here, the centre of the emitted light intensity distribution is shifted by several 10 nm to the right and left, respectively. Thus, these centres of the emitted light intensity distribution may only be taken as virtual positions of the dipole in x- and y-directions and not as its real position.

Figure 2:
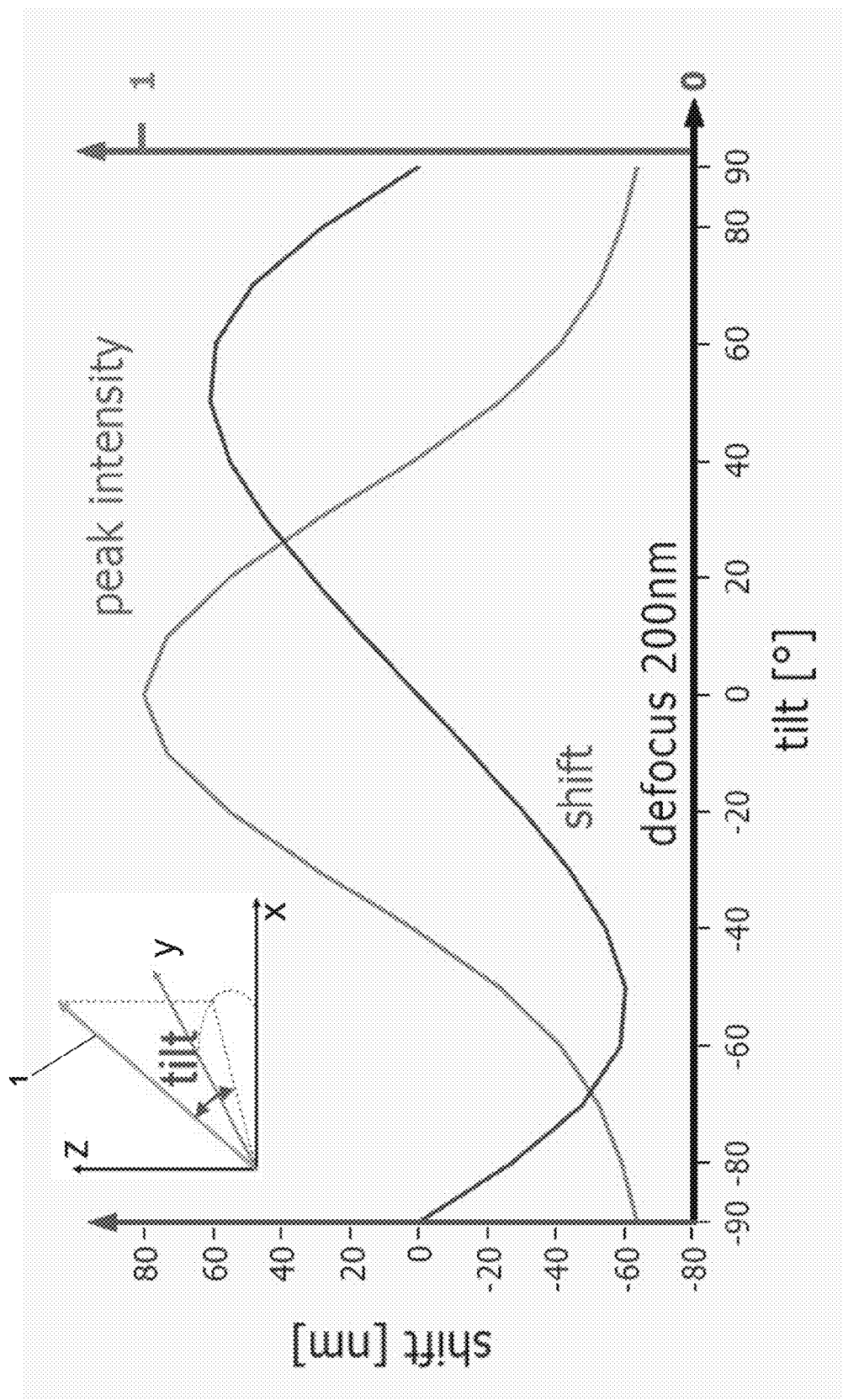
FIG. 2 is a plot of the virtual shift of a dipole tilted with regard to the x-y-plane by different angles from −90° to 90° when imaged with a defocus of 200 nm. Further, FIG. 2 indicates the peak intensity of the emitted light intensity distribution in the respective images of the dipole.

FIG. 2 is a plot of the shift of the virtual position of the dipole in x- and y-direction with regard to its real position in images of the dipole at a fixed defocus of 200 nm versus the tilt angle of the dipole with regard to the x-y-plane between −90° and +90°. The maximum shift occurs at about +50° and −50° and amounts to 60 nm. One may argue that such large shifts only occur with images showing a low peak intensity also depicted in FIG. 2. However, even with peak intensities of 50% of the maximum peak intensity, the shift amounts to ±40 nm.

Figure 3:
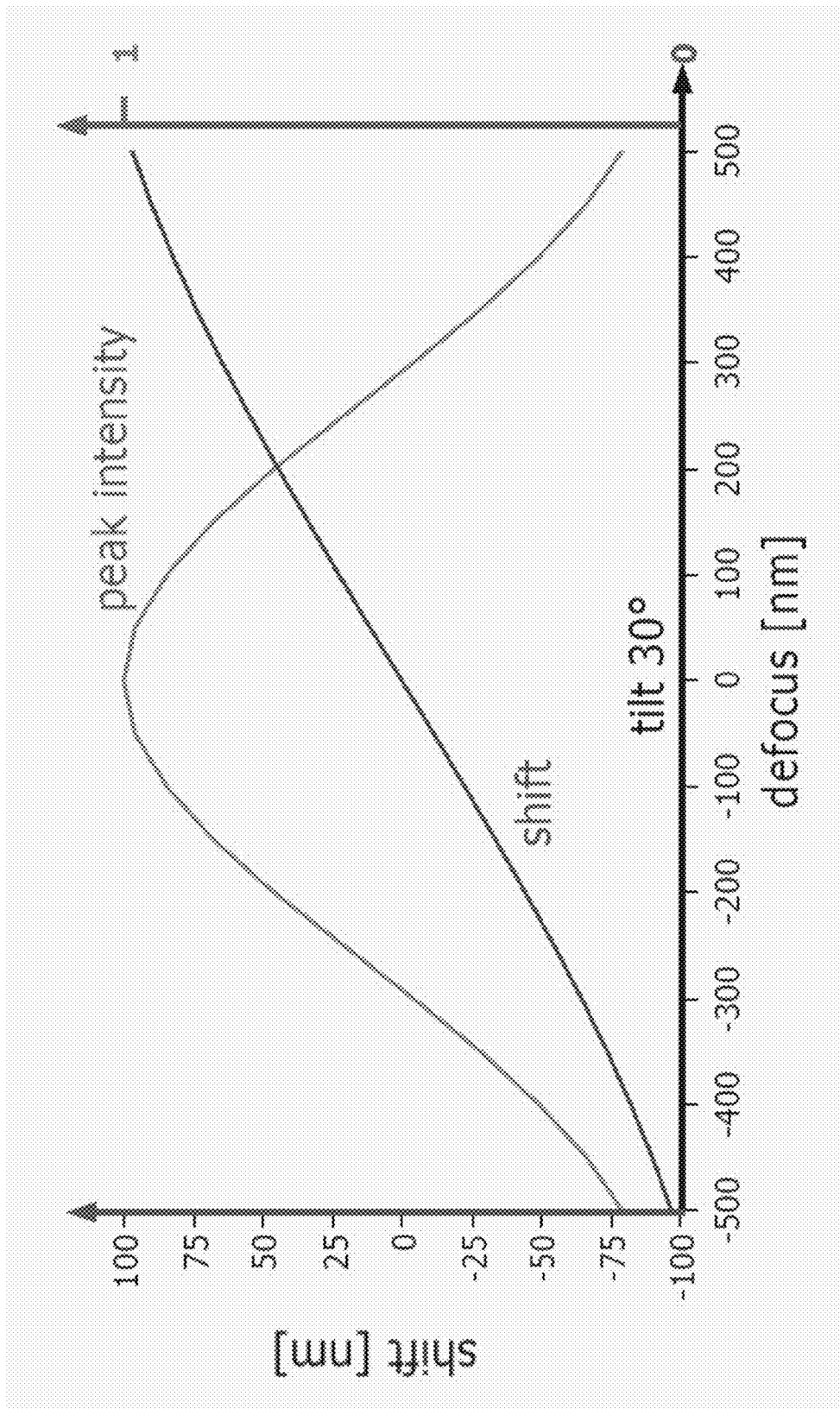
FIG. 3 is a plot of the virtual shift of the position of the dipole at a fixed tilt of 30° with regard to the x-y-plane versus a defocus of the images of the dipole from −500 to +500 nm. Further, FIG. 3 indicates the peak intensity of the emitted light intensity distribution in the respective images of the dipole.

The plot of FIG. 3 showing the shift of the virtual position of the imaged dipole in images of a varying defocus from −500 too +500 nm indicates that the shift about linearly varies with the defocus with a fixed tilt angle of the dipole with regard to the x-y-plane. This allows for a linear extrapolation of the virtual position of the dipole for a defocus of zero, where the shift is zero. The slope of the shift with regard to the defocus will be easily obtained from two images with a known difference in focus in axial- or z-direction. The real z-position of the dipole, at which the defocus would be zero may then be obtained from the absolute and relative peak emitted light intensities of the emitted light intensity distributions in the two images in combination with the slope of the shift. As a result, one will obtain the real position of the dipole in x- and y-direction, the real position of the dipole in z-direction and the orientation of the dipole with regard to the x-y-plane and with regard to both the x- and y-direction.

This method of determining the real position of a tilted dipole from at least two images 2 of the dipole 1 with two focal planes 13 at a known distance in the space of the dipole 1 is also illustrated in FIG. 4. FIG. 4 indicates five different focal planes 13 and the respective images 2 of the dipole, which is located in the middle focal plane 13, plus—by a dashed line—the peak emitted light intensity I(z) in the images 2 depending on the z-position of the focal plane 13. The virtual lateral positions of the images 2 of the dipole 1 are shifted by dx from focal plane 13 to focal plane 13 arranged at a distance dz. At the same time the peak emitted light intensity decreases from the middle plane toward the outer planes and the spot or image size increases. Evaluating all these available data (i.e. the virtual lateral positions, the peak emitted light intensity and the spot or image size of the images 2 of the dipole 1) from at least two images in two of the focal planes indicated in FIG. 4 allows for determining the real z-position of the dipole and for extrapolating the x- and y-position of the dipole for this z-position. i.e. for determining the real x- and y-position of the dipole. The z-position of the dipole may, for example, be determined in that a function I(z) is fitted to the measured values of the peak emitted light intensity I(z) in the images 2 of the dipole.

FIG. 4 discloses how the intensity distribution of fluorescence light emitted by a tilted dipole is three dimensionally distributed over different focal planes separated by dz. Thus, it explicitly shows the shift dx of the virtual x-position of the dipole derived from the centre of the intensity distribution over the respective focal plane from plane to plane, and the course of the peak intensity along z. The final evaluation for the real position of the dipole is standard arithmetics. An expert in the field may use proven methods such as fitting a Gaussian curve to the measured data or performing standard interpolation and extrapolation arithmetics.

Additionally FIG. 3 displays the dependencies between the defocus, the peak intensity and the shift. With that information an expert in the field is easily able to perform the required evaluation of actual image data for the real x-, y- and z-positions of an emitting dipole.

FIG. 5 illustrates an apparatus comprising an objective 3 for imaging light emitted out of a sample 4 onto a spatial light detector 5, which may be a CCD-camera. The apparatus according to FIG. 5 further comprises a beam splitter 6 for coupling activation light from an activation light source 7 into the objective 3, and a tube lens 8. However, the most important part of the apparatus according to FIG. 5 is an optical element 9 defining two regions 11 and 12 of the numerical aperture 10 of the objective 3. The region 11 is a ring shaped outer zone of the aperture 10 having a higher effective N.A., and the region 12 is a circular inner zone of the aperture 10 having a lower effective N.A. The regions 11 and 12 are separated from each other in that the optical element 9 causes a deflection of the light passing through the one of these two regions with regard to the light passing through the other one of these two regions. Thus, each light emitting object in the sample 4 imaged onto the spatial light detector 5 results in a double-image 2 with an offset 15 between its two partial images. An overall emitted light intensity distribution 14 detected with the spatial light detector 5 and depicted in FIG. 5 shows one double-image 2 of a light emitting dipole imaged in plane or in focus. Here, the two partial images made up from the light passing through the different regions 11 and 12 of the aperture 13 display a basic offset 15 only due to the deflection, and, besides the offset 15, both partial images are essentially identical. Further images 2' and 2", however, show increased offsets 15', and different partial images due to the different effective numerical apertures of the regions 11 and 12 having different effects on the images of light emitted by tilted dipoles. A complete evaluation of the two partial images of the double-image 2 of each light emitting dipole, including an account for the relative and/or absolute total or peak emitted light intensities, allows for determining the real x-, y- and z-positions of the dipole plus its tilt angle.

We claim:

1. A method of three-dimensionally localizing light emitting marker entities of unknown orientation and unknown position in a sample, the method comprising:

imaging light emitted by each single marker entity in at least two different ways onto at least one detection plane which corresponds to a focal plane in the sample resulting in at least two images of each marker entity;

separately determining virtual x- and y-positions in parallel to the focal plane of each marker entity from the emitted light intensity distribution over each image of each marker entity;

determining a z-position of each marker entity normal to the focal plane from the emitted light intensity distributions over the images of each marker entity; and determining real x- and y-positions of each marker entity in parallel to the focal plane based on its virtual x- and y-positions and on its z-position.

2. The method of claim 1, wherein the absolute and/or relative total or peak emitted light intensities in the images of each marker entity are accounted for in determining the z-position of each marker entity normal to the focal plane.

3. The method of claim 1, wherein emitted light intensity patterns in the images of each marker entity are accounted for in determining the z-position of each marker entity normal to the focal plane.

4. The method of claim 1, wherein a function $I(x,y,z,p)$ is fitted to the emitted light intensity distributions over the images of each marker entity, wherein p is the dipole direction of each light emitting marker entity.

5. The method of claim 1, wherein the light emitted by each single marker entity is imaged in at least two different ways resulting in at least two images of each marker entity in that each single marker entity is imaged onto at least two detection planes corresponding to at least two focal planes arranged at a known distance in the sample to provide the at least two images.

6. The method of claim 1, wherein the light emitted by each single marker entity is imaged in at least two different ways resulting in at least two images of each marker entity in that the light emitted by each single marker entity is separately imaged via at least two different aperture regions of a same objective onto the at least one detection plane to provide the at least two images.

7. The method of claim 1, wherein the real x- and y-positions of each marker entity in parallel to the focal plane are extrapolated for its z-position normal to the focal plane from its virtual x- and y-positions.

8. The method of claim 1, wherein a plurality of light emitting marker entities of unknown orientation in the sample is three-dimensionally localized based on an overall emitted light intensity distribution over the at least one detection plane detected during one period of time.

9. The method of claim 7, wherein the virtual x- and y-positions determined from the emitted light intensity distribution over the images of each marker entity are accounted for in determining the z-position of the molecule normal to the focal plane.

10. The method of claim 8, wherein different pluralities of light emitting marker entities of unknown orientation in the sample which are selected by a statistical transfer process between a light emitting state and a no or other light emitting state of the marker entities, are localized based on several overall emitted light intensity distributions over the at least one detection plane detected during different periods of time.

* * * * *